United States Patent [19]

Steinbiss et al.

[11] Patent Number: 5,238,847
[45] Date of Patent: Aug. 24, 1993

[54] TEST KIT AND PROCESS FOR THE DETERMINATION OF AN ANALYTE IN A PASTY SAMPLE

[75] Inventors: Joachim Steinbiss, Lorsch; Heinz-Friedrich Trasch, Ludwigshafen, both of Fed. Rep. of Germany

[73] Assignee: Boehringer Mannheim GmbH, Mannheim, Fed. Rep. of Germany

[21] Appl. No.: 655,179

[22] Filed: Feb. 12, 1991

Related U.S. Application Data

[63] Continuation of Ser. No. 193,371, May 12, 1988, abandoned.

[30] Foreign Application Priority Data

May 20, 1987 [DE] Fed. Rep. of Germany ....... 3716891

[51] Int. Cl.$^5$ ...................... G01N 1/34; G01N 33/68; G01N 33/72
[52] U.S. Cl. ........................................ 436/64; 422/58; 422/61; 422/100; 422/101; 435/4; 435/28; 435/810; 436/66; 436/88; 436/178
[58] Field of Search .................... 422/58, 61, 56, 100, 422/101; 435/28, 64, 810; 436/64, 66, 177, 178, 88

[56] References Cited

U.S. PATENT DOCUMENTS

| | | | |
|---|---|---|---|
| 3,620,677 | 11/1971 | Morison | 23/253 |
| 3,902,847 | 9/1975 | Busch et al. | |
| 3,980,437 | 9/1976 | Kishimoto et al. | 23/253 |
| 3,996,006 | 12/1976 | Pagano | 23/253 |
| 4,235,601 | 11/1980 | Deutsch et al. | 23/230 |
| 4,361,537 | 11/1982 | Deutsch et al. | 422/56 |
| 4,365,970 | 12/1982 | Lawrence et al. | 436/66 |
| 4,427,769 | 1/1984 | Adlercreutz et al. | 435/7 |
| 4,605,629 | 8/1986 | Lange | 436/166 |
| 4,668,619 | 5/1987 | Greenquist et al. | 435/7 |
| 4,742,002 | 5/1988 | Guadagno | 435/28 |
| 4,786,594 | 11/1988 | Khanna et al. | 435/7 |
| 4,789,629 | 12/1988 | Baker et al. | 435/7 |
| 4,806,312 | 2/1989 | Greenquist | 422/56 |
| 4,808,379 | 2/1989 | Wardlaw et al. | 422/56 |
| 4,849,173 | 7/1989 | Chang | 422/56 |
| 4,855,240 | 8/1989 | Rosenstein et al. | 436/514 |
| 4,857,453 | 8/1989 | Ullman et al. | 435/7 |

FOREIGN PATENT DOCUMENTS

| | | |
|---|---|---|
| 0070366 | 1/1983 | European Pat. Off. . |
| 0117689 | 9/1984 | European Pat. Off. . |
| 0279574 | 8/1988 | European Pat. Off. . |
| 2514511 | 4/1983 | France . |
| 90/13802 | 11/1990 | World Int. Prop. O. . |

OTHER PUBLICATIONS

Farr, "Immunologic Methods for Measuring Human Serum Albumin In the Stool" in Report of the Ross Conference on Pediatric Research 50: 87–89 (1965).

Primary Examiner—Robert J. Hill, Jr.
Attorney, Agent, or Firm—Felfe & Lynch

[57] ABSTRACT

The present invention provides a test kit and a process thereof for the determination of an analyte in a pasty sample, especially in faeces, containing a sample application region which has a sample layer with a sample field for the application of a sample. An analysis device with reagents is provided which reacts with the analyte and includes a component producing a detection signal. The sample layer includes a material which is capillary-active so that a liquid is transported therein by capillary action.

18 Claims, 2 Drawing Sheets

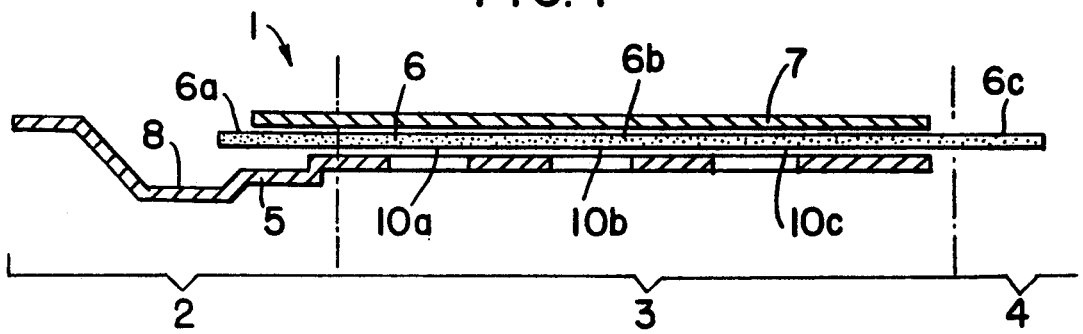
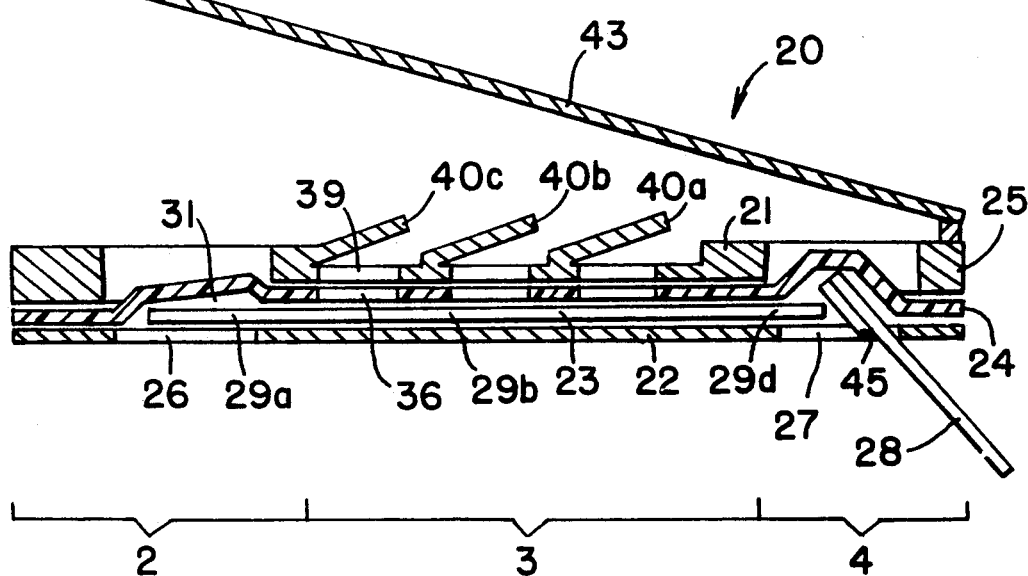
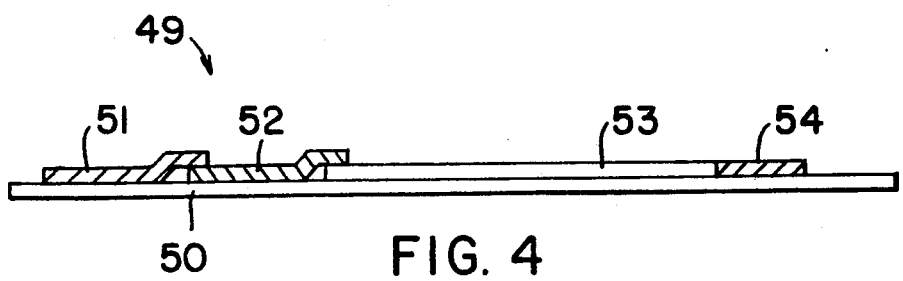

TEST KIT AND PROCESS FOR THE DETERMINATION OF AN ANALYTE IN A PASTY SAMPLE

This application is a continuation of application Ser. No. 193,371, filed May 12, 1988, now abandoned.

FIELD OF THE INVENTION

The present invention is concerned with a test kit for the determination of an analyte in a pasty sample containing a sample application means which has a sample layer with a sample field for the application of a sample and analysis means with reagents which react with the analyte and include a component producing a detectable signal. Furthermore, the present invention is concerned with a process for carrying out such a determination with such a test kit.

The most important field of use of the present invention is the analysis of faeces. Other sample materials for the analysis of which the present invention can advantageously be used include homogenisates of animal and human tissue samples, galenical slurries in the scope of pharmaceutical analysis and soil samples. In general, the present invention is especially suitable for the analysis of pasty, coatable samples which contain solid components. In the following, for the sake of simplicity but without limitation of the generality, reference is only made to the analysis of faeces.

BACKGROUND OF THE INVENTION

Test kits are frequently used for the determination of the presence or concentration of an analyte in faecal samples. In general, there are therewith meant combinations of reagents and adjuvants necessary for the analysis. A test kit usually consists of several units but one-piece analysis elements are also available for faecal investigations which are also to be regarded as being test kits within the meaning of the present invention.

The investigation of faeces for the presence therein of occult blood is of particular practical importance. In the scope of the measures for the early recognition of carcinomas and pre-cancerousness of the colon and rectum, the detection of occult blood represents the recognised method.

In the case of such wide-scale investigations, a simple handling of the test kit is especially important. At present, there are usually employed the so-called test sachets which, encompassed by a covering of cardboard, have a sample layer which usually includes paper impregnated with guaiac. After application of the sample to a sample field on the surface of the sample layer, the sachet is closed on the front side.

The evaluation is usually carried out by the physician in that a flap on the rear side of the sachet is opened and on to the rear side of the guaiac-impregnated paper is applied a developer solution which contains hydrogen peroxide. In the case of the presence of blood in the faeces, a colour change is thereby obtained.

Having regard to the fact that the blood content of the faeces is frequently not homogeneous, in general, double sachets are used on which, in each case, two samples are simultaneously applied from different places of the faeces. Furthermore, it is usual to use in a test kit three such sachets with which, on three successive days, the faeces are investigated. Insofar as only one of these samples is positive, further investigations are indicated.

These test sachets for the investigation of faeces for occult blood substantially fulfil the requirements for the handling of such a test. The handling steps to be carried out not only by the patients but also by the physician are relatively simple and the test takes place sufficiently quickly. The evaluation can take place without the help of apparatus and the production of the test kits is comparatively economic.

However, this simple handling was hitherto only achieved in the case of faecal blood tests with the help of guaiac papers. However, this has considerable diagnostic disadvantages. In particular, on the one hand, it is not sufficiently specific and, on the other hand, in many cases it is not sufficiently sensitive.

The deficient specificity is to be attributed to the fact that the detection method based on the pseudoperoxidase reaction of the haemoglobin also reacts on other components of the faeces, for example with animal blood introduced with the nutriments. In order to avoid falsely positive findings, the test must, therefore, be carried out with the use of a controlled diet.

Furthermore, there is knowingly used a relatively high sensitivity threshold. This in turn has the disadvantage that the danger exists that small blood concentrations, which are, nevertheless, clinically relevant, are overlooked so that falsely negative findings are obtained.

Because of these disadvantages, numerous attempts have already been made to use other test principles for the analysis of faecal components and especially for the detection of occult blood. Recently, immunological processes have, in particular, been suggested in which there are used binding components (Hb-antibodies) which are immunologically specific. However, such test kits are laborious to use.

In particular, the known immunological investigations of the faeces usually require laborious sample preparation measures. The sample must usually be homogenised, thereafter mixed with a liquid and finally centrifuged. Only the so produced pure supernatant can be used as sample liquid.

Under the trade name "Hemolex", there is known a test kit made by Orion, Finnland, for the immunological determination of haemoglobin in faeces which avoids centrifuging. Nevertheless, the procedure is very laborious. For example, the faeces must be homogenised immediately in a fresh state and taken up in a special solution. Insofar as this is not possible, the sample must be stored in a freezer.

From Federal Republic of Germany Patent Application No. 34 02 938, there is known a diagnostic aid for the immunological determination of haemoglobin in faeces in which a solid, rod-shaped carrier, which is coated with the antibody, is dipped directly into the faeces. The further evaluation requires several wet chemical steps, especially washings, and is, therefore, laborious.

From European Patent Specification No. 0,032,742, a test kit is known in which a formed body, preferably produced from synthetic resin, is used in the sample application region of which is present a filter paper impregnated with guaiac. However, this here not only serves for the detection but, at the same time, for filtering the sample. Whereas this is applied to the front side of the paper, on the rear side there is present an untreated filter paper. Due to the special construction of the formed body, it is possible to press together the sample, whereby the haemoglobin passes from the sample, together with liquid sample components, through the guaiac paper into the untreated filter paper. For the evaluation, the filter paper is removed and evaluated wet chemically.

It is an object of the present invention to provide a test kit and a process for the evaluation of faeces in which laborious handling steps, especially a preparation of the sample, are avoided.

SUMMARY OF THE INVENTION

Thus, according to the present invention, there is provided a test kit for the determination of an analyte in a pasty sample, especially in faeces, containing a sample application region which has a sample layer with a sample field for the application of a sample and an analysis means with reagents which react with the analyte and include a component producing a detection signal, wherein the sample layer consists of a material which is capillary-active so that a liquid is transported therein by capillary action. The sample layer is, on the one hand, in contact with an elution agent application region permitting liquid exchange so that an elution agent there applied penetrates into the sample layer and elutes an analyte contained in the sample which is soluble in the elution agent. On the other hand, the sample layer is in contact with an eluate take-up region permitting liquid exchange from which the elution agent is taken with the eluted analyte and passed to the analysis means.

The present invention also provides a process for the determination of an analyte in a sample, especially in faeces, with the use of a test kit according to the present invention, wherein a sample is applied to the sample layer, thereafter an elution agent is applied to the elution agent application region, waiting until the elution agent has flowed through the sample layer and has passed with the eluted analyte into the eluate take-up region, the eluate is brought into contact with the analysis means and, after formation of the detection signal, this is evaluated.

With the device according to the present invention and the corresponding process, it is possible to obtain a sample from faeces in a very simple way. Surprisingly, we have found that the elution agent is, on the one hand, able to dissolve the analyte from the faecal sample in a substantially reproducible way and to transport it into the detection region, whereas, on the other hand, practically no solid faecal components pass from the sample layer into the spatially separated elution agent take-up region.

As capillary-active within the meaning of the present invention, there are to be understood all layer materials which, on the basis of capillary-forming structures, have the ability of sucking up the liquid elution agent into the capillaries. Furthermore, the surface of the capillary-formed structures must be of a material which is wetted by the elution liquid. In addition, the material must, of course, be stable towards the aqueous elution solution preferably used and must not unfavourably influence the reaction.

As such materials, there can be used not only natural materials but also hydrophilic synthetic resins which, for the production of capillary-forming structures, are worked up to give papers, fleece, fabrics or appropriate porous or structured film.

In principle, it has proved to be sufficient when the sample is applied, for example, by coating on with a spatula, on to the sample field on the surface of the sample layer. Especially preferably, the sample layer is, however, in the region of the sample field so open structured that the sample penetrates at least partly therein. In this way, an improved elution of the analyte is achieved.

The contact between the elution agent application region and the sample layer, as well as between the sample layer and the detection region, which makes liquid exchange possible, can be achieved in various ways, for example in the form of slots or tubelets connecting the various regions. However, the sample layer is especially preferably a part of a larger liquid transport layer which, on the one hand, extends into the elution agent application region and, on the other hand, into the elution agent take-up region. Such an embodiment is especially simple to produce and is especially reliable in its function.

Surprisingly, we have found that, in the case of the test kit according to the present invention, it is not necessary to ensure that the faeces are analysed in a fresh state. Insofar as the faeces have to be stored for a comparatively long period of time, especially in the case of investigations extending over several days, it has even proved to be preferable to employ special measures in order to promote drying of the faeces.

The sample application region preferably includes several sample application fields separated from one another, this being achieved most preferably by providing only one sample layer upon which are present the sample fields. In practice, it has been shown that three faecal samples provided successively on a layer can be eluted sufficiently reproducibly so that, on the detection layer, a signal (especially a colour change) is produced insofar as only one of the samples contains the analyte. In this way, an integration of the analysis result over the three samples and thus an increase of the detection certainty is achieved.

With the test kit according to the present invention, there can be determined various components of the faeces (analytes) which are soluble in the elution agent. In particular, we have found that haemoglobin can thereby be determined as an indicator for occult blood. Other appropriate analytes include, for example, electrolytes, water-soluble proteins and enzymes, especially proteases.

However, the test kit has proved to be especially useful for the determination of human serum albumin. Within the scope of the present invention, we have found that human serum albumin is an outstandingly appropriate indicator for the presence of occult blood in faeces. In the case of a correct adjustment of the detection threshold (for example to about 0.1% v/w blood in the faeces, whereby, however, the appropriate value can be fixed empirically even more precisely), we have found that occult blood in faeces can be determined with albumin not only more specifically but also more sensitively than via the pseudo-peroxidase activity in the guaiac test or than in the immunological Hb determination. Thus, in all, there is given not only less falsely positive but also less falsely negative findings.

As detection reagents, there can be used numerous test systems commonly used in clinical chemistry for the particular analytes to be determined. The eluate take-up region can comprise an eluate take-up layer which, after it has been impregnated with eluate, can be taken and analysed wet chemically. However, especially preferably, the analysis means includes a test carrier with one or more reagent-containing test layers. Test carriers usually have a detection layer in which, at the end of the reaction in the detection layer, a signal-producing component is formed or passes therethrough. In this sense, there can, in principle, be used any signal which can be ascertained by measurement techniques, for example the radio-active emission of a radio-active labelling substance. However, the present invention is preferably directed towards tests which can be evaluated visually or with simple reflection photometric apparatus in which the signal consists of a colour change.

An immunological detection system is preferably used. We have found that the eluate is so substantially free of faecal components that, in spite of the extremely simple handling, there is achieved a sufficient preparation even for sensitive immunological determinations.

Especially for immunological processes of determination, it is advantageous when the test kit includes at least two parts separated from one another, namely, a sample collection unit and a detection unit. The detection unit is then produced and packed separately and first brought into contact with the sample layer permitting liquid exchange at the time of application of the elution agent. In the case of this embodiment, there is achieved an especially economical production and good storage stability, particularly of the detection unit.

BRIEF DESCRIPTION OF THE DRAWINGS

The present invention is explained in greater detail in the following, in conjunction with the embodimental examples illustrated schematically in the accompanying drawings, in which:

FIG. 1 is a cross-sectional view of a test kit according to the present invention;

FIG. 3 is a cross-sectional view of a sample collection unit according to FIG. 2 with a detection unit placed therein; and FIG. 4 is an alternative embodiment of a detection unit shown in a cross-sectional view.

DETAILED DESCRIPTION OF THE PREFERRED EMBODIMENTS

Figure 2:
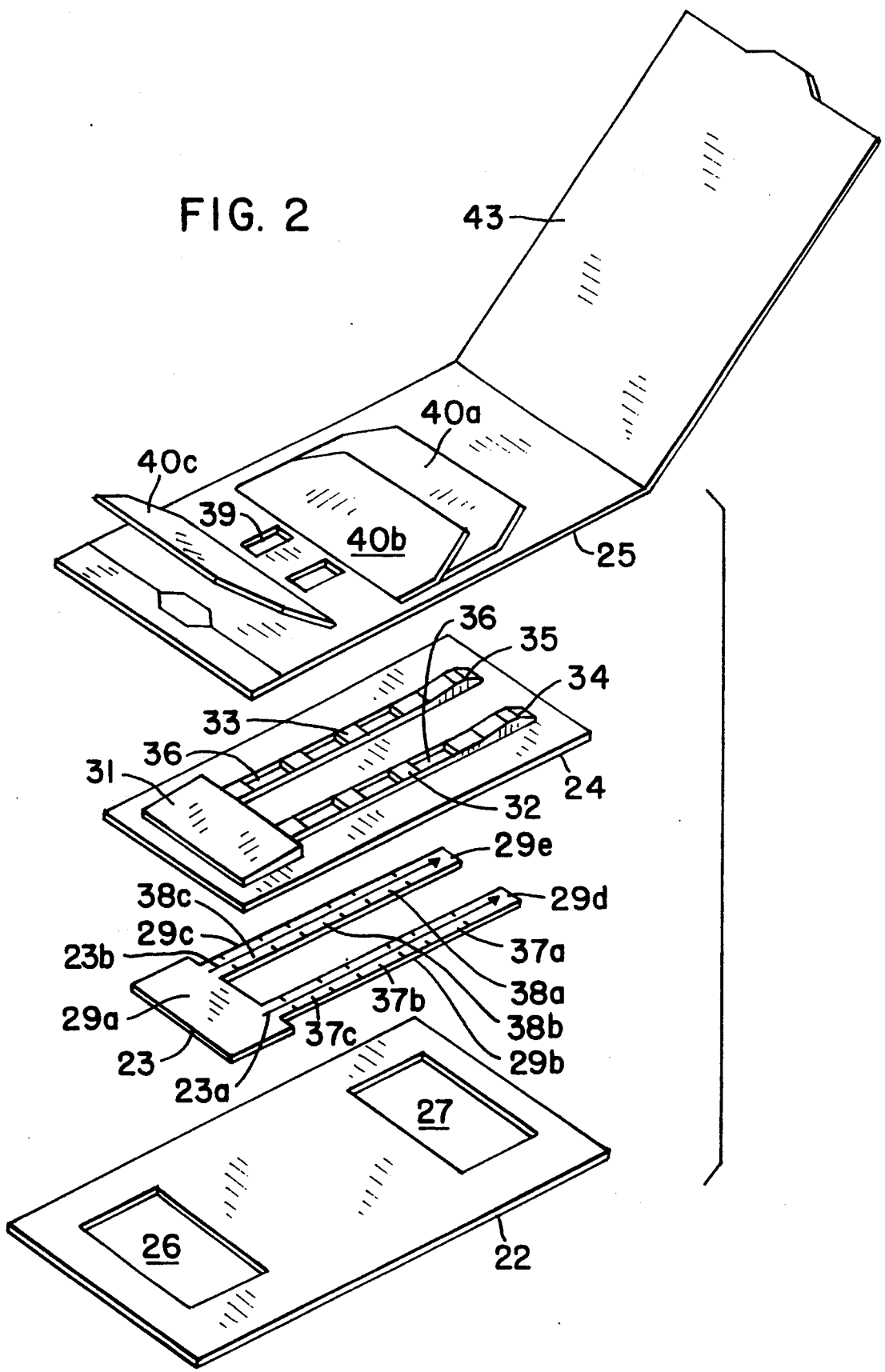
FIG. 2 is an exploded perspective view of a sample collection unit of a test kit according to the present invention.

The laboratory model illustrated in FIG. 1 of a test kit 1 can be divided up longitudinally into an elution agent region 2, a sample application region 3 and an eluate take-up region 4. It includes a synthetic resin base body 5, a continuous liquid transport layer 6 and a covering layer 7 arranged thereover and made, for example of synthetic resin.

In the elution agent application region 2, the synthetic resin base body 5 is formed into an elution agent trough 8. In the sample application region 3, it has three openings which surround sample fields 10a, 10b and 10c for three different faecal samples.

In the illustrated embodiment, the liquid transport layer 6 is a single continuous layer. In the elution agent application region 2, it forms a sucking up layer 6a for an elution agent introduced into the elution agent trough 8, in the sample application region 3 it forms a sample layer 6b with the sample fields 10a, 10b and 10c on its surface and in the eluate take-up region 4 it forms an eluate take-up layer 6c.

The illustrated embodiment with a continuous liquid transport layer is especially simple to produce. However, in the scope of the present invention, there can also be used separate layers 6a, 6b and 6c, the liquid exchange thereby being made advantageously possible in that these directly abut one another or mutually overlap.

For the application of the sample, the test kit is kept with the sample field upwardly (thus the reverse of what is illustrated). The faecal samples to be investigated are applied to the sample fields 10a, 10b and 10c in such a manner that, in each case, they at least cover the surface of the sample layer 6b and preferably partly penetrate into this layer 6b. The sample is thereafter allowed to dry.

For the evaluation, an elution agent, preferably water or an aqueous solution with adjuvant reagents, for example, wetting agents and buffers, is introduced into the elution agent through 8 or is dropped directly on to the sucking up layer 6a. The sucking up layer 6a sucks up the elution agent so that this passes from the elution agent application region 2 into the sample application region 3 and, always driven by capillary force, further into the eluate take-up region 4. In the sample application region 3, the elution agent dissolves the soluble analytes from the sample and transports them with it into the eluate take-up region 4. For practical purposes, this takes place sufficiently reproducibly whereas, at the same time, solid faecal components, which could disturb the detection, remain behind in the sample application region 3. Thus, there is provided an extremely simple sample preparation for the actual detection reaction which can be carried out in such a manner that the eluate is separately washed down from the eluate take-up layer 6c and is analysed in the liquid phase. However, the analysis preferably takes place with a test carrier, in which case the eluate take-up layer 6c can simultaneously serve as an eluate transfer means for transferring the eluate to a separate test carrier analysis means.

A part of the reagents necessary for the detection can, of course, already be present in the elution agent or in the liquid transport layer insofar as the action of these reagents is not disturbed by the presence of the faeces.

FIGS. 2 and 3 show an embodiment of the test kit of the present invention which is preferred and is simple to produce and which is especially suitable for the detection of occult blood in faeces in the scope of cancer care and, for this purpose, can be used to evaluate a total of six faecal samples collected on three successive days in an especially simple and precise manner.

The sample collection unit 21 of this test kit includes, running essentially parallel to each other a base part 22, an inert part 23, a synthetic resin formed part 24 and a covering part 25. In this case, too, the test kit 20 can be divided up into an elution agent application region 2, a sample application region 3 and an eluate take-up region 4.

The base part 22 can be produced, for example, from water-resistant cardboard and has two openings 26 and 27 through which the elution agent can be introduced or a detection unit 28 can be introduced into the sample collection unit 21.

The insert part 23 contains two liquid transport paths indicated by the arrows 23a and 23b. They are formed in the elution agent application region by a common elution agent sucking-up layer 29a which, in the sample application region 3, passes over into two separate sample layers 29b and 29c. The sample layers 29b and 29c pass, in turn, over into the eluate take-up layers 29d and 29e.

The illustrated one-piece embodiment of the insert part 23 is, in the same way as in the case of the liquid transport layer 6 according to FIG. 1, especially preferred but here, too, there can be used separate layers which are in liquid contact with one another.

In the synthetic resin formed part 24 are formed an elution agent trough 31, two liquid transport canals 32 and 33 and two take-up depressions 34 and 35 for, in each case, one detection unit 28. The liquid transport canals 32 and 33 have openings 36 through which samples can be applied to the sample layers 29b and 29c. The sample fields 37a, 37b, 37c, and 38a, 38b, 38c, on the sample layers 29b and 29c, which are framed by the openings 36, are, for the sake of clarity, indicated in FIG. 2 by broken lines.

The covering part 25 can again be made of water-resistant cardboard. It has openings 39 which are aligned with the openings 36 of the liquid transport canals 32 and 33. Three flaps 40a, 40b and 40c serve as covering elements in order to close off the applied samples in an odourless and hygienic manner. On the lower side of the flaps is applied an adhesive layer which ensures a dependable closure of the flaps.

On the other hand, the connection between the parts 22, 23, 24 and 25 is intentionally not made to be completely tight so that moisture from the applied sample can slowly escape, whereby this dries out.

The whole faecal collection element can additionally be closed with a closure flap 43. The inner side of the closure flap 43 preferably simultaneously serves as a carrier for printed operating instructions.

The test kit according to FIGS. 2 and 3 is used in such a manner that the flap 40a is first opened and two samples from different parts of the faeces are applied to the underlying sample fields 37a and 38a. Thereafter, the flap 40a is closed. In an analogous manner, on the following days, in each case two samples from different places of the faeces are applied to the sample fields 37b and 38b or 37c and 38c lying below the flaps 40b and 40c and the flaps 40b and 40c thereafter closed.

After all the samples have been applied, the closure flap 43 is closed and the sample collection unit is subsequently brought to the physician for the purpose of analysis.

For the analysis, in the medical laboratory the sample collection unit 21 is held with the openings 26 and 27 above. Through the opening 27 there is introduced into the reception recesses 34 and 35 in each case a detection unit in the form of a test carrier. The test carrier illustrated in FIG. 3 has a single test layer 45. Thereafter, elution agent is introduced through the opening 26 into the elution agent trough.

Because of the capillary forces acting in the layers 29a, 29b, 29d and 29a, 29c and 29e, the elution agent flows, analogously to the embodiment of FIG. 1, along the liquid transport paths 23a and 23b into the elution agent take-up region 4, whereby, in the sample application zone 3, it dissolves the analyte from the sample and transports it along.

In the case of the embodiment illustrated in FIGS. 2 and 3, the sample collection unit 21 is separate from the detection unit 28. For the analysis, it is, therefore, necessary that the eluate passes over from the eluate take-up layers 29d and 29e at the end of the liquid transport paths 23a and 23b to the test carrier 28. Preferably, this passing simply takes place by bringing the test layer 45, as is illustrated in FIG. 3, into contact with the end of the elution agent take-up layer 29d or 29e. However, there can also be provided a special transfer arrangement, for example, an additional fleece for the transfer of the eluate to the test carrier 28.

The test layer 45 of the test carrier 28 can contain all the reagents necessary for the analysis, including the components producing a detection signal. Thus, for example, there can take place in it an enzymatic reaction specific for the analyte which leads directly or indirectly to a colour change on the surface of the test field. Such reactions are known in numerous variants and do not need to be described here in detail.

The test kit according to FIGS. 2 and 3 is especially suitable for analyses with the help of an immunological test system. In this case, too, a single test layer can be used, as is explained hereinafter in more detail with reference to Example 4.

However, in the case of the use of an immunological test system for the detection of an analyte, there is especially preferred a test carrier construction such as is illustrated in principle in FIG. 4. Such a test carrier 49 basically includes a base layer 50 and several layers 51, 52, 53 and 54 arranged thereon next to one another, which are in liquid contact with one another. The liquid contact can thereby be achieved in that the edges abut one another or in that the layers mutually slightly overlap. The elution agent here fulfils a double function. It serves not only for the preparation of the sample in the sample collection unit 21 but also for the evaluation in the test carrier 49.

The test carrier 49 has a special take-over layer 51, the absorptive properties of which are such that it sucks up especially readily reproducibly the eluate from the eluate take-up layer 29d.

The test carrier is especially preferably constructed for analyses which follow the so-called IEMA principle. In this case, it contains successively a conjugate layer 52 with a first binding component in soluble form which is specific for the analyte and is labelled with a labelling enzyme, a solid phase binding layer 53 with the analyte or an analyte analogue and a signal forming layer 54 with a component giving a signal depending upon the presence of the labelling enzyme.

If, for example, the analyte is an antigen, then on the conjugate layer 52 is present an enzyme-labelled antibody for this antigen. The solid phase binding layer 53 contains the antigen or an antigen analogue, thus a substance which, in turn, is specifically bindable with the antibody from the layer 51, in carrier-fixed form. In this case, the signal-forming layer 54 can contain a colour-forming substrate for the labelling enzyme which, in the presence of the enzyme, undergoes a change involving a colour change.

If a test carrier according to FIG. 4 is used in a sample collecting unit according to FIG. 3, then the eluate first passes over into the transfer layer 51 and then migrates, driven by capillary forces, slowly through the layers 52, 53 and 54. The conjugate in the layer 52 is thereby dissolved, whereby the antibody present thereon in excess binds with the antigen. Not only the complexes formed but also excess antibody migrate further to the layer 53. The antibody excess there binds to the carrier-fixed antigen, whereas the complexes remain mobile and can pass into the signal forming layer 53. The colour change there taking place corresponds to the enzyme concentration and thus to the concentration of the analyte antigen.

Such a course of a test is, in principle, known. Further details are described, for example, in Federal Republic of Germany Patent Application No. 36 38 654 and in the publications mentioned therein. As is there described in detail, it is, in general, important so to construct immunochemical test carriers that the various analysis steps take place clearly and chronologically separate from one another. In the scope of the present invention, we have, however, found that, for the purposes of faecal analyses with the test kit according to the present invention, a simpler test carrier construction according to FIG. 4, in which the eluate can, without special control means, pass over from one layer into the next, is sufficient.

The following Examples are given for the purpose of illustrating the present invention:

EXAMPLE 1

Immunochemical determination of human blood components in faecal samples by analysis of human serum albumin (HSA)

On the sample fields 10a, 10b, 10c of a test kit according to FIG. 1 were, in each case, placed three faecal samples and these then dried overnight. The sample layer consisted of paper VS 532 of the firm Binzer, Hatzfeld, Federal Republic of Germany, with the following composition: 20% linters, 30% staple fibre, 10% Kuralon and 40% polyamide.

There was used 150 μl. of elution agent (PBS buffer; 150 mM sodium chloride and 50 mM potassium phosphate; pH 7.4).

As soon as the liquid front had reached the end of the eluate take-up layer 6c, this was cut off and investigated with an enzyme immune test (EIA) for HSA.

The HSA test tool place as follows:
the cut off eluate take-up layer was eluted for 10 minutes in 500 μl. PBS (phosphate buffered saline);
250 μl. of the eluate were incubated for 60 minutes in microtitre plates loaded with 10 μg. anti>HSA<IgG per well;
the wells were washed three times with PBS+0.05% w/v of Tween 20 (a non-ionic detergent of Atlas-Chemie, Essen, Federal Republic of Germany);
subsequently, 300 μl. anti HSA Fab-β-galactosidase conjugate were added per well, followed by shaking for 30 minutes;
the wells were washed as described above;
after the addition of 300 μl. chlorophenol red-galactoside (0.25 mM in 10 mM potassium phosphate, 25 mM sodium chloride and 5 mM magnesium chloride; pH 7.6) per well, the plates were shaken for 10 minutes and subsequently the reacted substrate was measured at 577 nm in a microtitre plate photometer;
the absolute values were determined from a series of standard solutions tested simultaneously.

The following Table 1 shows the results obtained. In the upper line, there is thereby given in which of the sample fields 10 there was introduced a faecal sample with 0.1% v/w blood admixture and in the second line there is given the amount determined in the case of the measurement.

TABLE 1

| | position of the faecal sample(s) with 0.1% blood admixture | | | | | | | |
|---|---|---|---|---|---|---|---|---|
| | 1 | 2 | 3 | 1 + 2 | 2 + 3 | 1 + 3 | 1 + 2 + 3 | control |
| ng. HSA | 60 | 80 | 60 | 110 | 120 | 100 | 170 | <5 |

In the case of the control experiment, 3 faecal samples were used without the admixture of blood.

The results show that the HSA values determined are substantially independent of the position of the blood-containing faecal samples and are proportional to the total number of blood-containing samples. Thus, there is achieved a dependable analysis and especially a dependable detection of occult blood in faeces.

EXAMPLE 2

Detection of occult blood in faeces based on guaiac

As in Example 1, faecal samples were introduced into a test kit according to FIG. 1 and dried. As eluate take-up layer there was so incorporated a guaiac-impregnated paper from a commercially available faecal blood test (hemoFec of Boehringer Mannheim GmbH, Mannheim, Federal Republic of Germany) that a liquid exchange with the sample layer 6b was possible. As before, the analyte was eluted from the samples and the guaiac-impregnated paper moistened with the eluate was sprinkled with a conventional developer solution containing hydrogen peroxide and the test evaluated visually.

The results obtained are given in the following Table 2, the various lines thereby giving the results with the blood concentrations indicated in each case at the beginning of the line. The last column shows the results obtained with a commercially available hemoFec test.

TABLE 2

| % v/w blood/faeces | position of the faecal sample(s) with blood admixture | | | | | | | |
|---|---|---|---|---|---|---|---|---|
| | 1 | 2 | 3 | 1 + 2 | 2 + 3 | 1 + 3 | 1 + 2 + 3 | hemoFec |
| 0.1% | − | − | − | − | − | − | − | − |
| 0.6% | − | − | − | + | + | + | + | − |
| 1.0% | − | +− | +− | + | + | + | ++ | +− |
| 2.0% | + | + | + | ++ | ++ | ++ | ++ | + |

+ = clearly positive indication
− = clearly negative indication
+− = doubtful value
++ = a coloration showing a high blood concentration especially clearly.

It can be seen that the sensitivity in the case of only one blood-containing sample in the test does not suffer in comparison with the commercially available hemoFec test. It is thus shown that the peroxidate blood components detected with guaiac are sufficiently quantitatively eluted.

It is of especial importance that, in the case of the presence of at least two blood-containing samples, the sensitivity of the test is substantially increased so that, even in the case of the use of a guaiac detection system, falsely negative findings are avoided.

EXAMPLE 3

Determination of HSA or of occult blood with a test kit according to FIGS. 2 and 3 with the use of a test carrier according to FIG. 4

The transfer layer 51 has a surface area of 6×6 mm. and consists of untreated paper VS 532 of the firm Binzer, Hatzfeld, Federal Republic of Germany.

The conjugate layer 52 has a size of 10×6 mm. and consists of a multifilar polyester fabric 2F 777 of the Schweizer Seidengaze Fabrik, Thal, Switzerland. The fabric is impregnated with a solution of Fab-$\beta$-galactosidase conjugate.

The solid phase binding layer 53 and the signal-forming layer 54 consist in all of a porous nylon membrane "Biodyne BNRG 0.2 $\mu$m" of the firm Pall, Dreieich, Federal Republic of Germany.

HSA is fixed on the solid phase binding layer 53. For this purpose, the membrane is placed overnight in a solution with an HSA concentration of 10 mg./ml. HSA which is buffered with 50 mM potassium phosphate (pH 7.4) and 150 mM sodium chloride. On the next day, it is washed three times with the same buffer but without HSA and dried.

The signal-forming layer 54 is additionally impregnated with chlorophenol red-galactoside (CPRG).

The so constructed test carrier is used in the same manner as described in connection with FIGS. 2–4. HSA contained in the eluate reacts in the conjugate layer 52 with the there impregnated anti-HSA-$\beta$-galactosidase conjugate. Only the so formed complexes are able to migrate to the solid phase binding layer 53 and to react with the CPRG contained in the signal-forming layer 54.

The total passage of the elution agent through the sample collection unit 21 and the test carrier 49 takes about 5 to 7 minutes. Within the course of 10 to 15 minutes, the colour of the substrate changes so that a visual evaluation can be made. The presence of HSA is indicated by a red coloration.

Serial experiments with such test kits have shown that, in the case of an adjusted detection limit of 0.5% blood in the faeces, surprisingly there are ascertained not only less falsely negative findings but also less falsely positive findings. The latter is especially surprising because, in the case of the previously used test principles, high detection limits were always adjusted in order to avoid too many falsely positive findings.

EXAMPLE 4

Detection of HSA with a sandwich EIA

A test carrier was used which, corresponding to FIG. 3, had a single test field. This consisted of a nylon membrane (Pall Biodyne 1.2 $\mu$m.) which, by incubation overnight in 10 mg. antibody/ml., 50 mM potassium phosphate/150 mM sodium chloride (pH 7.4) and washing three times with 50 mM potassium phosphate/150 mM sodium chloride, was adsorptively loaded with anti<human haemoglobin>-IgG (polyclonal).

The test carrier moistened with the eluate was taken and washed with running tap water with liquid excess. Subsequently, it was adjusted in a wash buffer with 150 mM sodium chloride, 50 mM potassium phosphate (pH 7.4), 0.05% Tween 20 and 1 mU/ml. anti<hHB>-$\beta$-galactosidase conjugate for about 1 minute and briefly stirred therein several times. Thereafter, the test field was again washed under running water and placed directly into a CPRG-containing substrate solution. A colour reaction on the membrane dependably showed the presence of blood in the faecal samples.

The terms and expressions which have been employed are used as terms of description and not of limitation, and there is no intention in the use of such terms and expressions of exluding any equivalents of the features shown and described or portions thereof, it being recognized that various modifications are possible within the scope of the invention.

We claim:

1. Test kit for determination of an analyte in a pasty, solid and liquid containing sample comprising:

(a) a sample collection unit including (i) a base means, (ii) a covering means, (iii) an insert means positioned in between said base means and said covering means, said base means, covering means and insert means being in an essentially parallel arrangement, (iv) means for supplying an elution agent, and (v) means for receiving an eluate, wherein said insert means and said means for supplying an elution agent are in fluid communication with each other and said insert means and said means for receiving an eluate are in fluid communication with each other, said means for supplying an elution agent, said insert means and said means for receiving an eluate defining a transport path for a liquid to flow in a direction parallel to said insert means wherein:

one of said covering means and base means defines a sample application point for application of a sample to said insert means, said application point being defined by an opening in one of said covering means and base means, said opening being of sufficient size for a pasty, solid and liquid containing sample to be applied to and to cover a sample field surface of said insert means exposed by said opening, said insert means includes means for receiving a sample via said opening, wherein said means for receiving a sample is made of capillary active material, said means for supplying an elution agent comprises a material which takes up an elution agent and transports it to said insert means, said means for receiving an eluate comprises a material which takes up a liquid from said insert means and comprises a transfer means for transferring said liquid to a separate test carrier analysis means; and (b) a test carrier analysis means which is a structure separate from and unconnected to said sample collection unit, said separate test carrier analysis means including a base means and at least one reagent layer which contains a reagent system which generates a detectable signal in the presence of the analyte to be determined.

2. Test kit of claim 1 wherein said covering means is sufficiently loosely connected in said sample collection unit as to permit evaporation of moisture.

3. Test kit of claim 1, wherein said one of said covering means or base means comprises a plurality of openings positioned consecutively therein along said transport path.

4. Test kit of claim 1, wherein said elution agent application means, insert means and eluate reception means define two transport paths.

5. Test kit of claim 4, wherein one of said covering means or base means defines three openings for sample application to each of said transport paths.

6. Test kit of claim 5, wherein said covering means defines three openings and is further characterized by three flap means which, in down position, close said openings.

7. Test kit of claim 6, further comprising a closure flap connected to said covering means at one end.

8. Test kit of claim 1, wherein said analysis means comprises an immunological test system.

9. Test kit of claim 1, wherein said analysis means comprises a reagent system for detecting human serum albumin for determination of occult blood in feces.

10. Test kit of claim 1, said test carrier analysis means comprising a plurality of layers positioned on said base means and in fluid contact with each other.

11. Test kit of claim 10 wherein said plurality of layers comprises:
    (i) a first layer containing an enzyme labelled component which specifically binds to the analyte to be determined,
    (ii) a second layer containing solid phase bound analyte or analyte analogue, and
    (iii) a third layer containing a component which forms a detectable signal in the presence of the labelling enzyme, wherein said first, second and third layer are arrayed to permit flow of a liquid from said first layer into said second layer and from said second layer into said third layer.

12. Test kit of claim 1, wherein said opening is positioned in said covering means, and said covering means is further characterized by a flap means which, in down position closes said opening.

13. Test kit of claim 12, further comprising a closure flap connected to said covering means at one end.

14. Method for diagnosis of a disease wherein occult blood is found in feces, comprising contacting a fecal sample to the kit of claim 1, adding an elution agent to said elution agent application means, and measuring human serum albumin in the eluate as an indication of said disease.

15. Method of claim 14 wherein said disease is a cancer.

16. Method for determining an analyte in a pasty, solid and liquid containing sample comprising:
    contacting said pasty, solid and liquid containing sample to the means for receiving a sample of the sample collection unit of claim 1 to penetrate into said capillary active material,
    introducing a liquid elution agent to said means for supplying an elution agent so as to transport said elution agent from said means for supplying an elution agent through said means for receiving a sample, so as to form an eluate containing said analyte,
    said eluate flowing essentially parallel to said means for receiving a sample and perpendicular to said direction of said penetration of said sample into said means for receiving an eluate, and
    transferring said eluate by said transfer means to said separate test carrier analysis means and determining said analyte in said separate test carrier analysis means.

17. Method of claim 16, wherein said analyte is human serum albumin.

18. Method of claim 16, further comprising drying said sample prior to introduction of said elution agent.

* * * * *